US012773483B2

(12) United States Patent
Chen

(10) Patent No.: US 12,773,483 B2
(45) Date of Patent: Oct. 27, 2026

(54) BREAST PUMP

(71) Applicant: SHENZHENSHI LUTEJIACHENG SUPPLYCHAIN MANAGEMENT CO., LTD., Shenzhen City (CN)

(72) Inventor: Wanyuan Chen, Shenzhen City (CN)

(73) Assignee: SHENZHENSHI LUTEJIACHENG SUPPLYCHAIN MANAGEMENT CO., LTD., Shenzhen (CN)

( * ) Notice: Subject to any disclaimer, the term of this patent is extended or adjusted under 35 U.S.C. 154(b) by 753 days.

(21) Appl. No.: 18/138,070

(22) Filed: Apr. 22, 2023

(65) Prior Publication Data

US 2024/0001011 A1 Jan. 4, 2024

Related U.S. Application Data

(63) Continuation-in-part of application No. 17/962,556, filed on Oct. 10, 2022, now Pat. No. 12,576,193.

(30) Foreign Application Priority Data

Jul. 4, 2022 (CN) ......................... 202221735508.2

(51) Int. Cl.
*A61M 1/06* (2006.01)

(52) U.S. Cl.
CPC ............ *A61M 1/069* (2021.05); *A61M 1/064* (2014.02)

(58) Field of Classification Search
CPC ............................................ A61M 1/06–0697
See application file for complete search history.

(56) References Cited

U.S. PATENT DOCUMENTS

| | | | | |
|---|---|---|---|---|
| 8,118,772 | B2 * | 2/2012 | Dao | A61M 1/06 604/74 |
| 11,554,198 | B1 | 1/2023 | Pan | |
| 11,554,199 | B1 | 1/2023 | Chen | |
| 11,806,454 | B2 * | 11/2023 | De Becdelievre | A61M 1/067 |
| 2014/0094748 | A1 | 4/2014 | Hong et al. | |
| 2015/0217034 | A1 * | 8/2015 | Pollen | A61M 1/064 604/74 |
| 2016/0296682 | A1 | 10/2016 | Phillips et al. | |
| 2022/0265907 | A1 | 8/2022 | Hwang | |

* cited by examiner

*Primary Examiner* — Courtney Fredrickson

(57) ABSTRACT

A breast pump is provided, including a milk bowl, and a breast shield detachably connected to the milk bowl, and a main body detachably connected to the milk bowl. A milk storage cavity for storing milk is defined by the milk bowl and the breast shield. The main body includes a housing detachably connected to the milk bowl, and an air pump disposed in the housing and used for generating negative pressure. The milk bowl is provided with a milk outlet spatially communicating with the milk storage cavity, and the housing is provided with a hole plug engaged to the milk outlet and used for partially sealing or completely sealing the milk outlet when the housing is assembled with the milk bowl.

11 Claims, 11 Drawing Sheets

BREAST PUMP

FIELD OF THE DISCLOSURE

The present disclosure relates to the technical field of breast pumps, and more particularly to a breast pump.

BACKGROUND OF THE DISCLOSURE

The breast pump is used to assist lactating women to pump the milk in the breast and store the milk in a milk collector, so as to solve the problem of breastfeeding for lactating women. The breast pump is mainly composed of a milk bowl and a main body. A vacuum pump in the main body can provide negative pressure for the milk collector so that the milk bowl can pump the milk in the breast.

However, in the existing breast pumps, external foreign matter is easy to fall into the milk storage cavity through the milk outlet, which affects the quality of milk, and is in urgent need of improvement.

SUMMARY OF THE DISCLOSURE

The purpose of the present disclosure is to provide a breast pump for the defects and deficiencies of the prior art, which has the advantage of preventing external foreign matter from falling into a milk storage cavity through a milk outlet, and ensuring that milk is not polluted.

For achieving the aforementioned purpose, the technical solution adapted by the present disclosure is to provide a breast pump, including a milk bowl, a breast shield detachably connected to the milk bowl, and a main body detachably connected to the milk bowl. A milk storage cavity for storing milk is defined by the breast shield and the milk bowl. The main body includes a housing detachably connected to the milk bowl, and an air pump disposed in the housing and used for generating negative pressure. The milk bowl is provided with a milk outlet spatially communicating with the milk storage cavity, and the housing is provided with a hole plug engaged to the milk outlet and used for partially sealing or completely sealing the milk outlet when the housing is assembled with the milk bowl.

In preferred embodiments, when the breast shield is configured to attach to a breast, the milk outlet faces upward.

In preferred embodiments, the milk outlet is arranged on an outer edge of the milk bowl.

In preferred embodiments, the milk outlet has an inner wall surface that is arc-shaped, and the hole plug has an outer wall surface that is arc-shaped and corresponds to the milk outlet.

In preferred embodiments, the milk outlet is semi-cylindrical shaped, and the hole plug is semi-cylindrical shaped.

In preferred embodiments, when the housing is assembled with the milk bowl, an outer wall surface of the hole plug is spaced apart from an inner wall surface of the milk outlet.

In preferred embodiments, the housing is provided with a positioning groove, the hole plug extends from a groove bottom of the positioning groove, the milk bowl is provided with a hole wall forming the milk outlet, and when the housing is assembled with the milk bowl, the hole plug is engaged to the milk outlet, and the hole wall is engaged to the positioning groove.

In preferred embodiments, when the housing is assembled with the milk bowl, the hole wall fits into the positioning groove.

In preferred embodiments, a side wall of the positioning groove is arc shaped, and an outer wall surface of the hole wall has an arc-shaped outer wall surface corresponding to the side wall of the positioning groove.

In preferred embodiments, the positioning groove is semi-cylindrical shaped, and the hole wall is semi-cylindrical shaped corresponding to the side wall of the positioning groove.

In preferred embodiments, the side wall of the positioning groove is provided with a positioning rib, and when the hole plug is inserted into the milk outlet, the positioning rib abuts against the outer wall surface of the hole wall.

By virtue of the above technical solution, the present disclosure has the beneficial effects as follows. In the present disclosure, the hole plug is provided on the housing, so that when the milk bowl is assembled with the main body, the hole plug seals or partially seals the milk outlet of the milk bowl, which helps to prevent the external foreign matter from falling into the milk storage cavity through the milk outlet, ensuring that the milk is free from contamination and also helps prevent the milk in the milk storage cavity from spilling when the user shakes it.

BRIEF DESCRIPTION OF THE DRAWINGS

In order to more clearly illustrate the technical solutions in the embodiments of the present disclosure or the prior art, the following will briefly introduce the drawings that need to be used in the description of the embodiments or the prior art. Obviously, the accompanying drawings in the following description are only some embodiments of the present disclosure. For those skilled in the art, other drawings can also be obtained according to these drawings without any creative effort.

Figure 1:
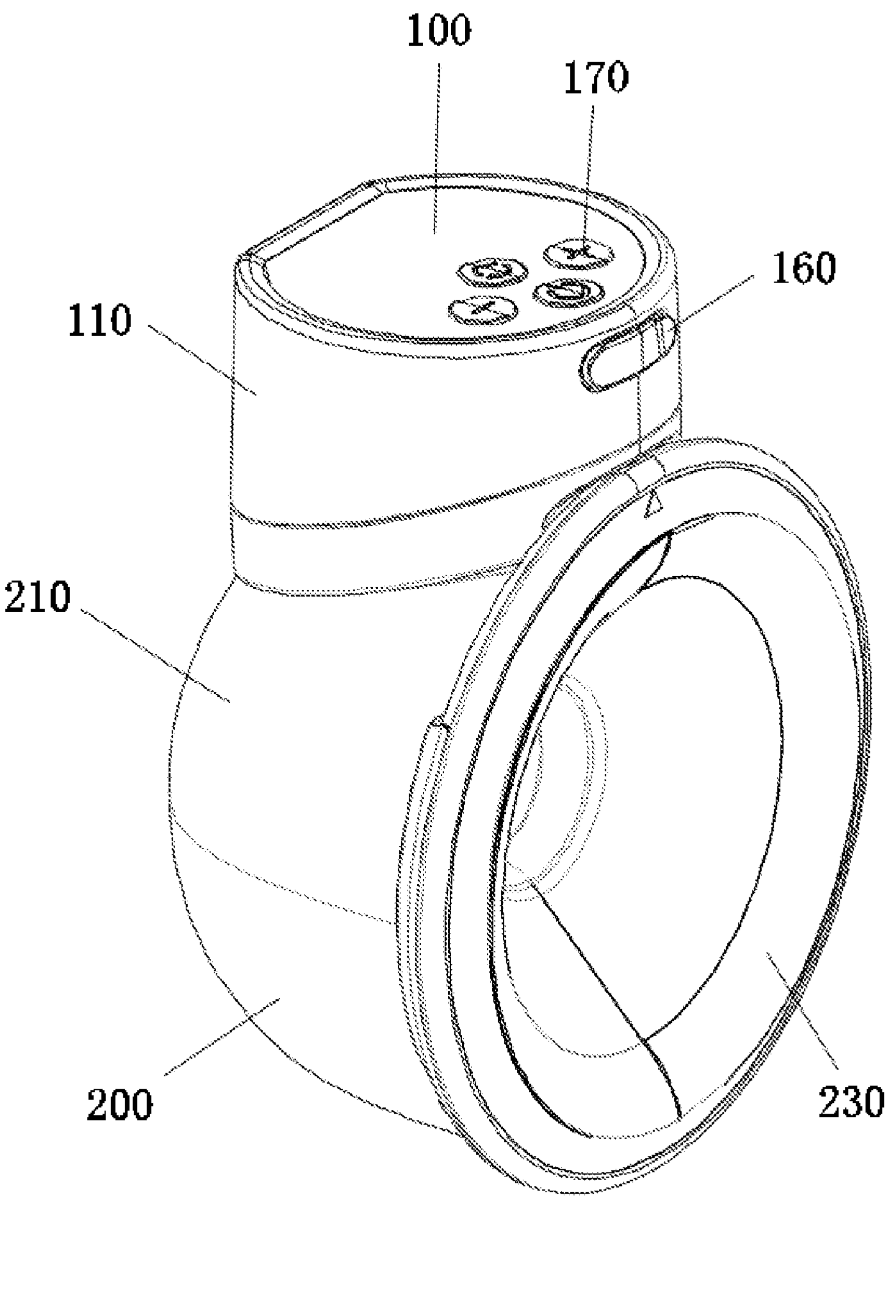
FIG. 1 a schematic structural diagram of a breast pump when a main body and a milk collector are in a combined state.

Reference numeral: 100, main body; 110, housing; 111, connecting groove; 112, elastic protrusion; 113, spring groove; 114, arc-shaped protrusion; 115, charging hole; 116, hole plug; 117, positioning groove; 118, positioning rib; 120, circuit board; 121, charging member; 130, air pump; 140, pressure relief valve; 150, battery; 160, dust plug; 170, button; 171, switch key; 172, mode key; 173, gear increase key; 174, gear reduce key; 180, elastic sealing member; 200, milk collector; 210, milk bowl; 211, connecting post; 212, groove; 213, arc-shaped groove; 214, placement plane; 215, clamping flange; 216, milk outlet; 217, hole wall; 220, milk storage cavity; 230, breast shield; 231, connector; 232, sealing ring; 233, mounting groove; 234, liquid inlet groove; 240, airway connector; 241, suction port; 242, milk flowing port; 243, negative pressure port; 250, one-way valve; 260, membrane; 300, ventilation tube; a, first surface; b, second surface; c, third surface; d, fourth surface.

DETAILED DESCRIPTION OF THE EXEMPLARY EMBODIMENTS

The present disclosure will be described in further detail below in conjunction with the accompanying drawings.

The specific embodiment is only an explanation of the present disclosure, and is not a limitation of the present invention. Those skilled in the art can make modifications to the embodiment as required after reading the specification, and as long as they are within the rights of the present modifications to the embodiment, all claims are protected by the patent law.

The present embodiment relates to a breast pump, which is used to assist a lactating woman to pump the milk in her breast and store the milk.

Reference is made to FIG. 1, in which the breast pump includes: a milk collector 200 and a main body 100. The main body 100 is detachably connected to the milk collector 200.

Figure 2:
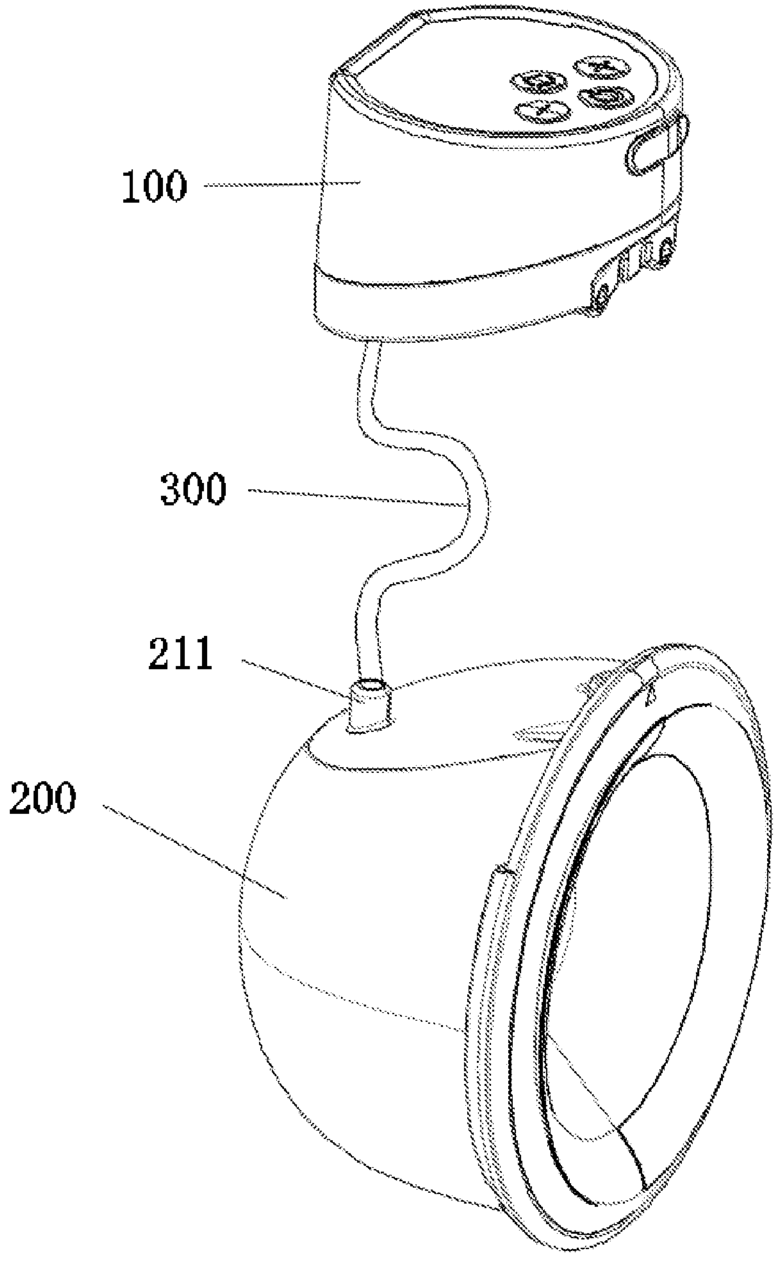
FIG. 2 is a schematic structural diagram of the main body and the milk collector being connected through a ventilation tube in a detached state.

As a preferred embodiment, as shown in FIG. 2, the breast pump further includes a ventilation tube 300, and two ends of the ventilation tube 30 are detachably and respectively connected to the main body 100 and the milk collector 200.

Figure 3:
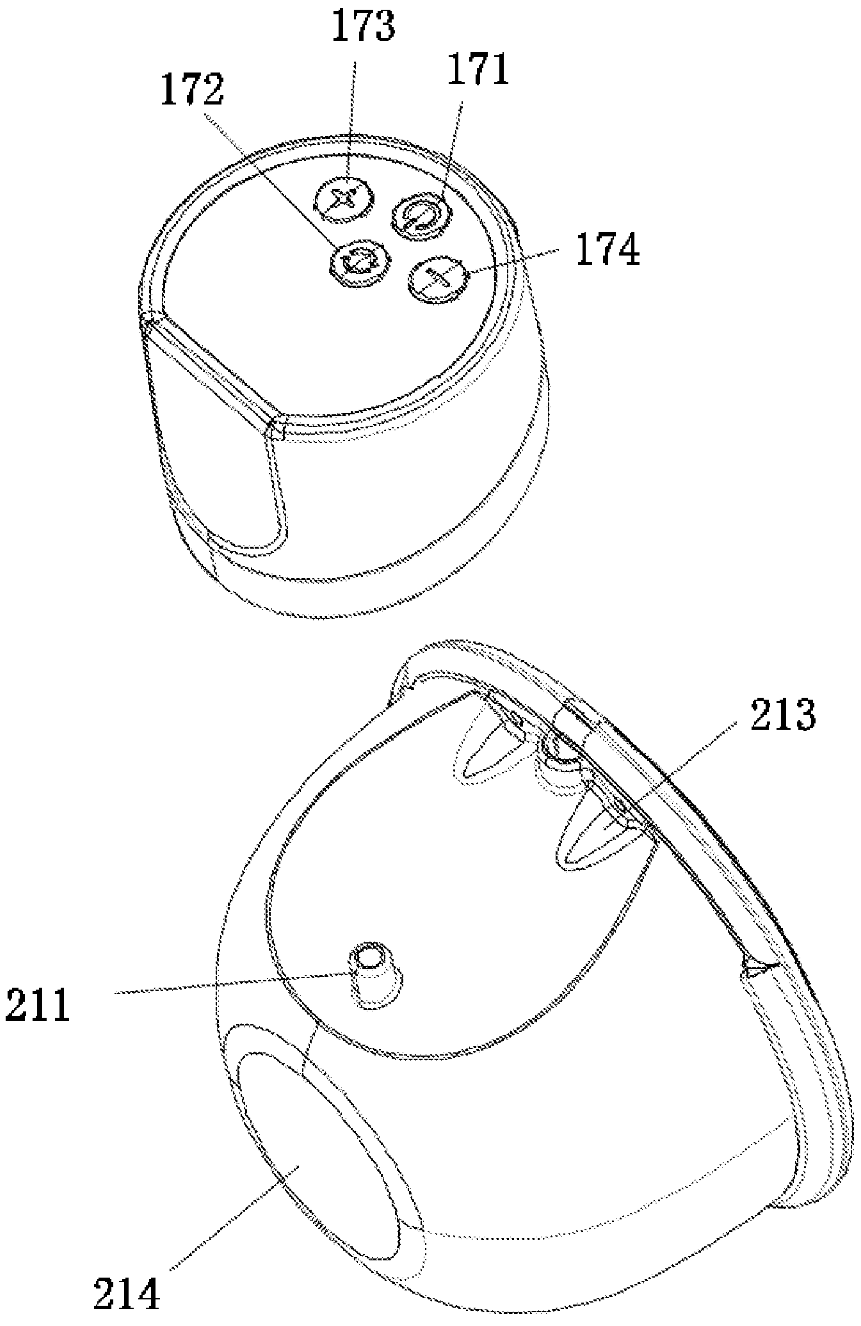
FIG. 3 is a schematic structural diagram of the main body and the milk collector in a detached state.

The breast pump mainly has two usage states, one is a combined state as the breast pump shown in FIG. 1, and the other is a detached state as the breast pump shown in FIG. 2 and FIG. 3. The main body 100 of the breast pump in the combined state is connected to the milk collector 200. After the main body 100 is connected to the milk collector 200, the main body 100 can directly form negative pressure on the milk collector 200, so that the milk collector 200 can pump milk from a breast. When the main body 100 and the milk collector 200 are connected to each other, the breast pump can be directly put into the breastfeeding underwear, which is more convenient to use. The main body 100 of the breast pump in the detached state spatially communicates with the milk collector 200 through the ventilation tube 300. The milk collector 200 is placed on the breast. The main body 100 can be worn on a wearer's waist or head. The main body 100 forms the negative pressure on the milk collector 200 through the ventilation tube 300, so that the milk collector 200 pumps the milk from the breast, and the breast pump in the detached state can avoid a weight of the main body 100 from being loaded on the milk collector 200, thereby avoiding excessive weight on user's breasts. Therefore, a user can selectively switch the breast pump between the detached state and the combined state according to the actual situation. The breast pump has strong compatibility and provides good user experience.

Figure 4:
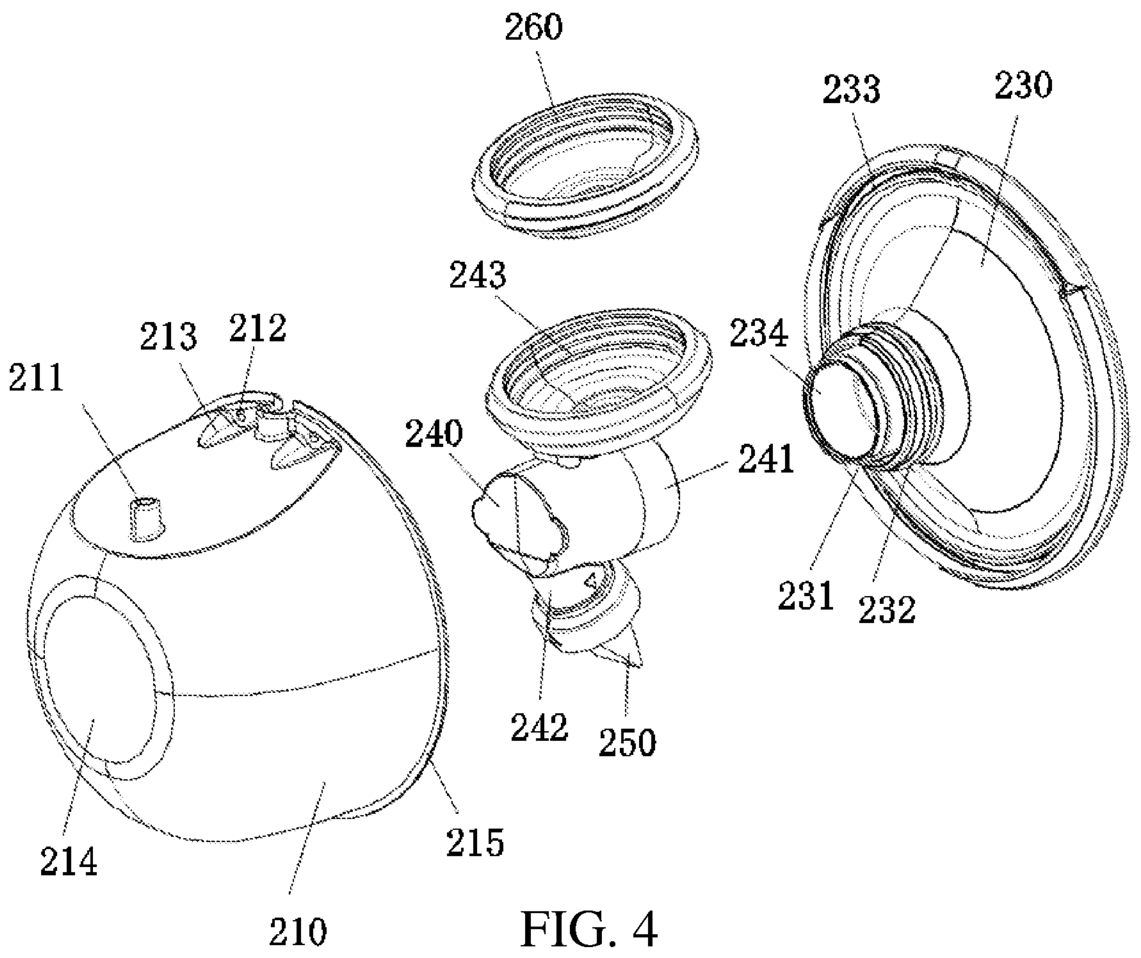
FIG. 4 is a schematic structural exploded diagram of the milk collector.
Figure 6:
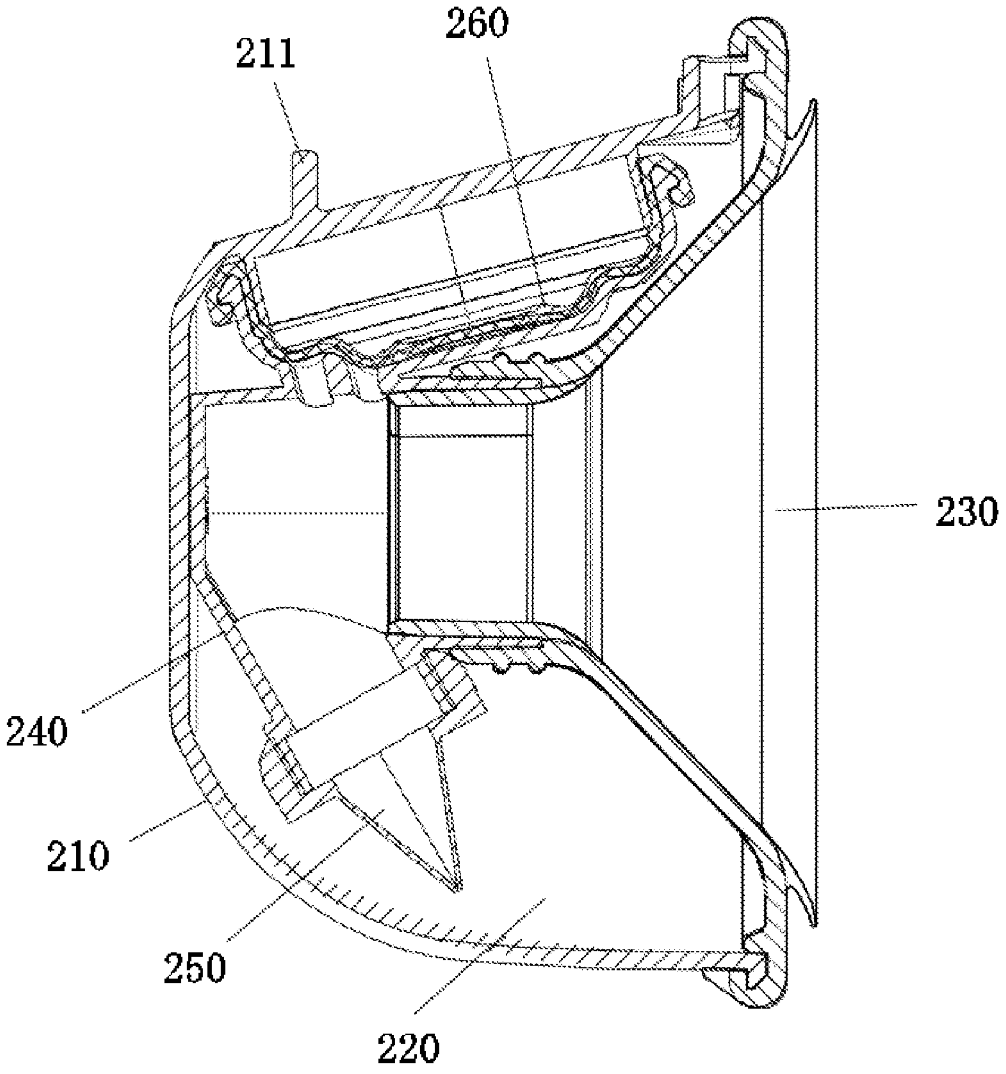
FIG. 6 is a sectional view of the milk collector.

Reference is made to FIG. 4 and FIG. 6, in which the milk collector 200 includes a milk bowl 210, a breast shield 230 detachably connected to the milk bowl 210 such that a milk storage cavity 220 for storing milk is defined by the breast shield 230 and the milk bowl 210, an airway connector 240 disposed in the milk storage cavity 220, a membrane 260 that is elastically deformable and a one-way valve 250. The airway connector 240 has a suction port 241, a milk flowing port 242 and a negative pressure port 243 that are in communication with each other. The suction port 241 is connected to the breast shield 230, the milk flowing port 242 is connected to the one-way valve 250, and the negative pressure port 243 is connected to the membrane 260. A function of the one-way valve 250 is to make the milk flow in one direction from the airway connector 240 to the milk storage cavity 220.

Figure 5:
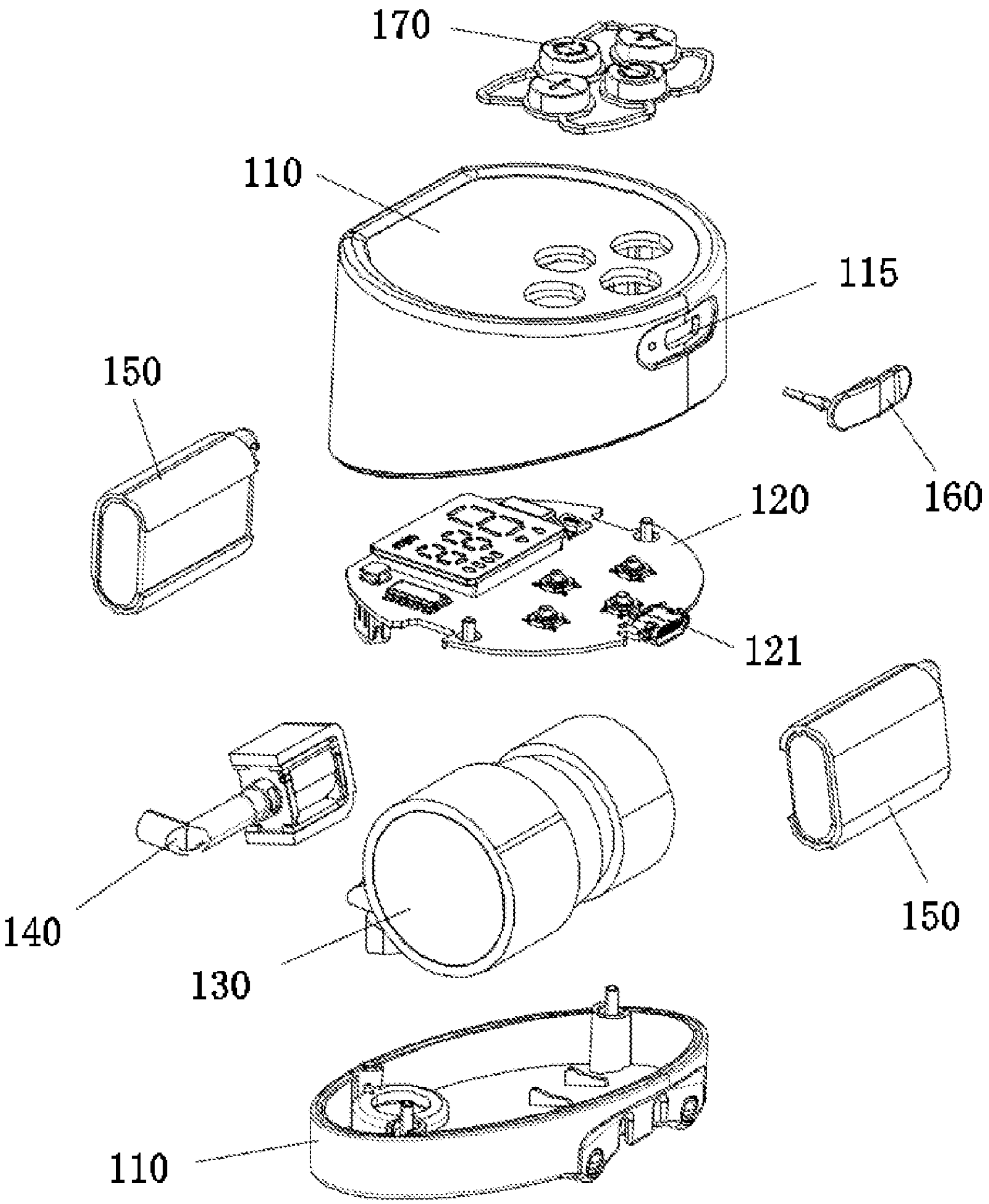
FIG. 5 is a schematic structural exploded diagram of the main body.

Referring to FIG. 5, the main body 100 includes: a housing 110 detachably connected to the milk bowl 210, a circuit board 120 disposed in the housing 110, an air pump 130 for generating the negative pressure on the membrane 260, a pressure relief valve 140 for restoring the air pressure of a space between the membrane 260 and the milk bowl 210, and a battery 150 for supplying power.

The air pump 130 and the pressure relief valve 140 are spatially communicated with the membrane 260. Specifically, an inlet end of the air pump 130 is in spatial communication with the membrane 260, and an outlet end of the pressure relief valve 140 is in spatial communication with the membrane 260. When working, the air pump 130 draws air, so that a side of the membrane 260 facing away from the air pump generates the negative pressure, which acts on the breast through the negative pressure port 243 and the suction port 241. The breast secretes milk under the action of negative pressure, and the milk in the user's breast flows to the milk storage cavity 220 from the one-way valve 250 through the suction port 241 and the milk flowing port 242. After the air pump 130 stops pumping air, the pressure relief valve 140 takes in air, so that the air pressure on the side of the membrane 260 away from the air pump returns to a normal pressure state.

There are two batteries 150 respectively disposed on two sides of the air pump 130 for powering the negative air pump 130. In the present embodiment, the air pump 130 is a diaphragm pump. In other embodiments, the air pump 130 may also be a piston pump.

Figure 10:
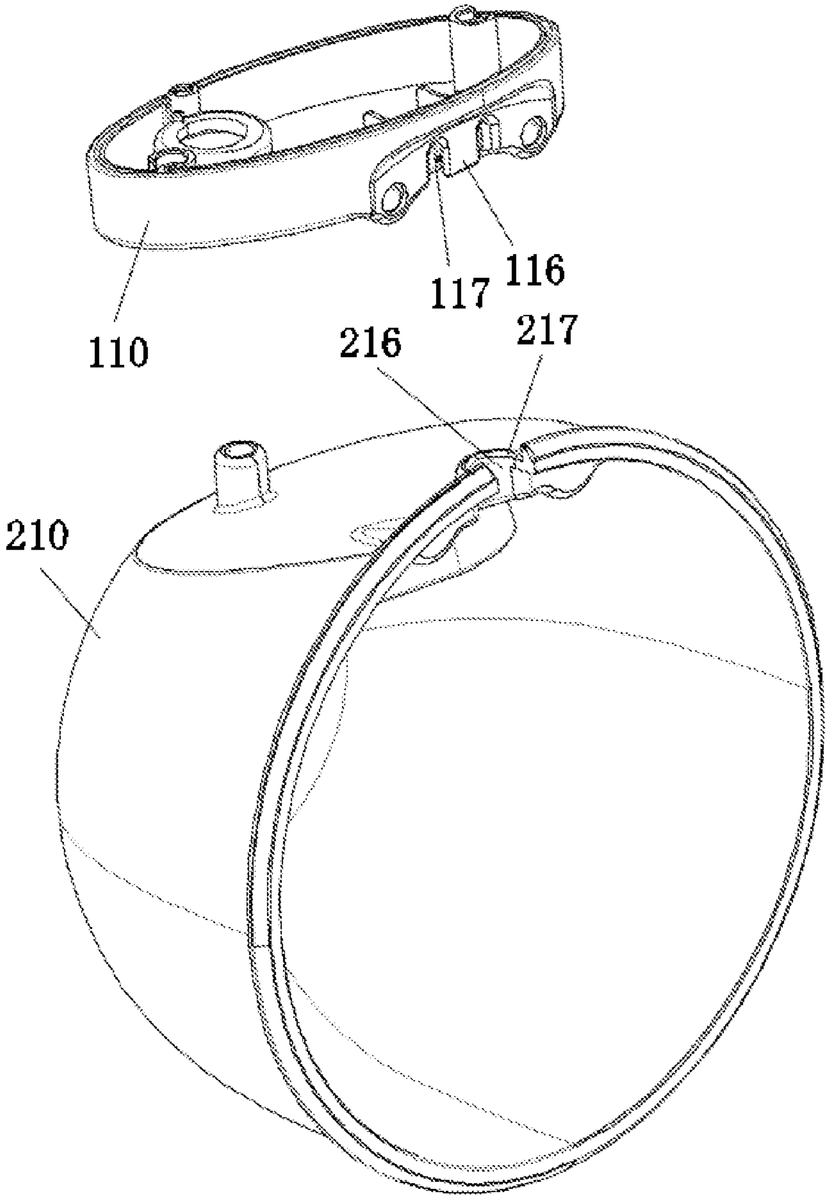
FIG. 10 is a schematic structural diagram of yet another perspective of the housing and the milk bowl.

In the present embodiment, as shown in FIG. 10, the milk bowl 210 is provided with a milk outlet 216 spatially communicating with the milk storage cavity 220, and the housing 110 is provided with a hole plug 116 which can be engaged to the milk outlet 216 when it is assembled with the milk bowl 210, and is used for partially sealing the milk outlet 216. When the milk bowl 210 is attached to the breast, the milk outlet 216 faces upward. By setting the hole plug 116 on the housing 110, when the milk bowl 210 is assembled with the main body 100, the hole plug 116 partially seals the milk outlet 216 of the milk bowl 210, which helps to prevent external foreign matter from falling into the milk storage cavity 220 through the milk outlet 216, and ensures that the milk is not polluted. In addition, it also helps to prevent the milk in the milk storage cavity 220 from spilling out when the user shakes it. When the milk bowl 210 is attached to the breast, the setting of the milk outlet 216 facing upward makes the milk not overflow from the milk outlet 216 when the breast pump is working.

In the present embodiment, the hole plug 116 partially seals the milk outlet 216 of the milk bowl 210, leaving a ventilation channel through which the outside air communicates with the milk storage cavity 220, so as not to affect the flow of milk into the milk storage cavity 220. In some embodiments, the hole plug 116 can be configured to fully seal the milk outlet 216, but it is necessary to provide a ventilation channel at other positions of the milk bowl 210 to spatially communicate the milk storage cavity 220 with outside air.

In the present embodiment, as shown in FIG. 10, the milk outlet 216 is disposed on an outer edge of the milk bowl 210. The milk outlet 216 has an arc-shaped inner wall surface, and the hole plug 116 has an arc-shaped outer wall surface corresponding to the milk outlet 216. The milk outlet 216 is arranged on the outer edge of the milk bowl 210 and has an arc-shaped inner wall, so that the user can pour out the milk stored in the milk storage cavity 220 along the arc-shaped inner wall of the milk outlet 216.

More specifically, the milk outlet 216 is in a semi-cylindrical shape, and the hole plug 116 is also in the semi-cylindrical shape.

When the housing 110 is assembled with the milk bowl 210, the outer wall of the hole plug 116 is spaced apart from the inner wall of the milk outlet 216, so as to leave the ventilation channel through which the outside air communicates with the milk storage cavity 220.

In the present embodiment, as shown in FIG. 10, the housing 110 is provided with a positioning groove 117, the hole plug 116 extends from a groove bottom of the positioning groove 17, and the milk bowl 210 is provided with a hole wall 217 forming the milk outlet 216. When the housing 110 is assembled with the milk bowl 210, the hole plug 116 is inserted into the milk outlet 216, and the hole wall 217 is inserted into the positioning groove 117, so that the cooperation between the hole plug 116 and the milk outlet 216 is more stable.

In a preferred embodiment, the sidewall of the positioning groove 117 is arc-shaped, and the outer wall of the hole wall 217 has an arc-shaped outer wall corresponding to the sidewall of the positioning groove 117.

In a preferred embodiment, the positioning groove 117 is in the semi-cylindrical shape, and the hole wall 217 is in the semi-cylindrical shape corresponding to the side wall of the positioning groove 117.

Figure 11:
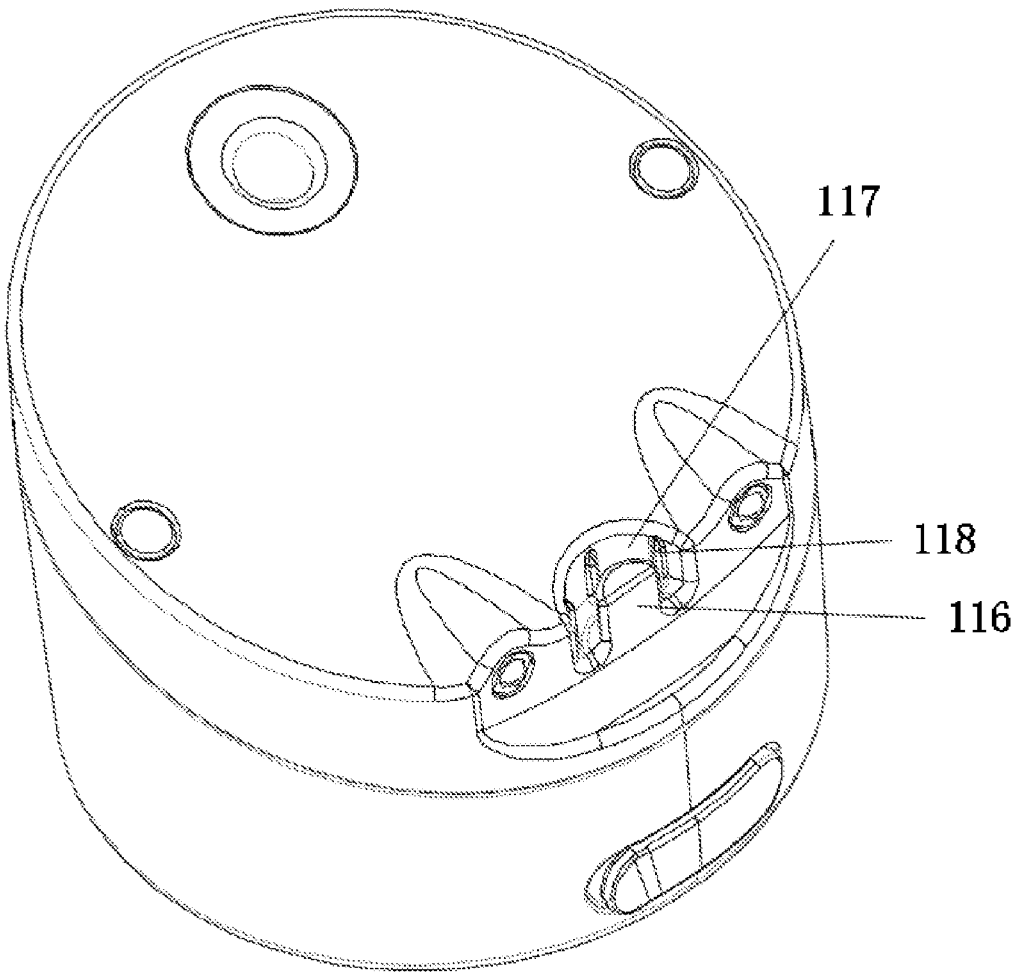
FIG. 11 is a schematic structural diagram of the main body.

As shown in FIG. 11, the side wall of the positioning groove 117 is provided with a positioning rib 118, so that when the hole plug 116 is inserted into the milk outlet 216, the positioning rib 118 abuts against the outer wall surface of the hole wall 217, and the assembly of the hole plug 116 and the milk outlet 216 becomes tighter. In the present embodiment, there are three positioning ribs 118, which are distributed on the sidewall of the positioning groove 117 with equal arcs. In other embodiments, other numbers of positioning ribs 118 can be provided, preferably two or more.

Figure 7:
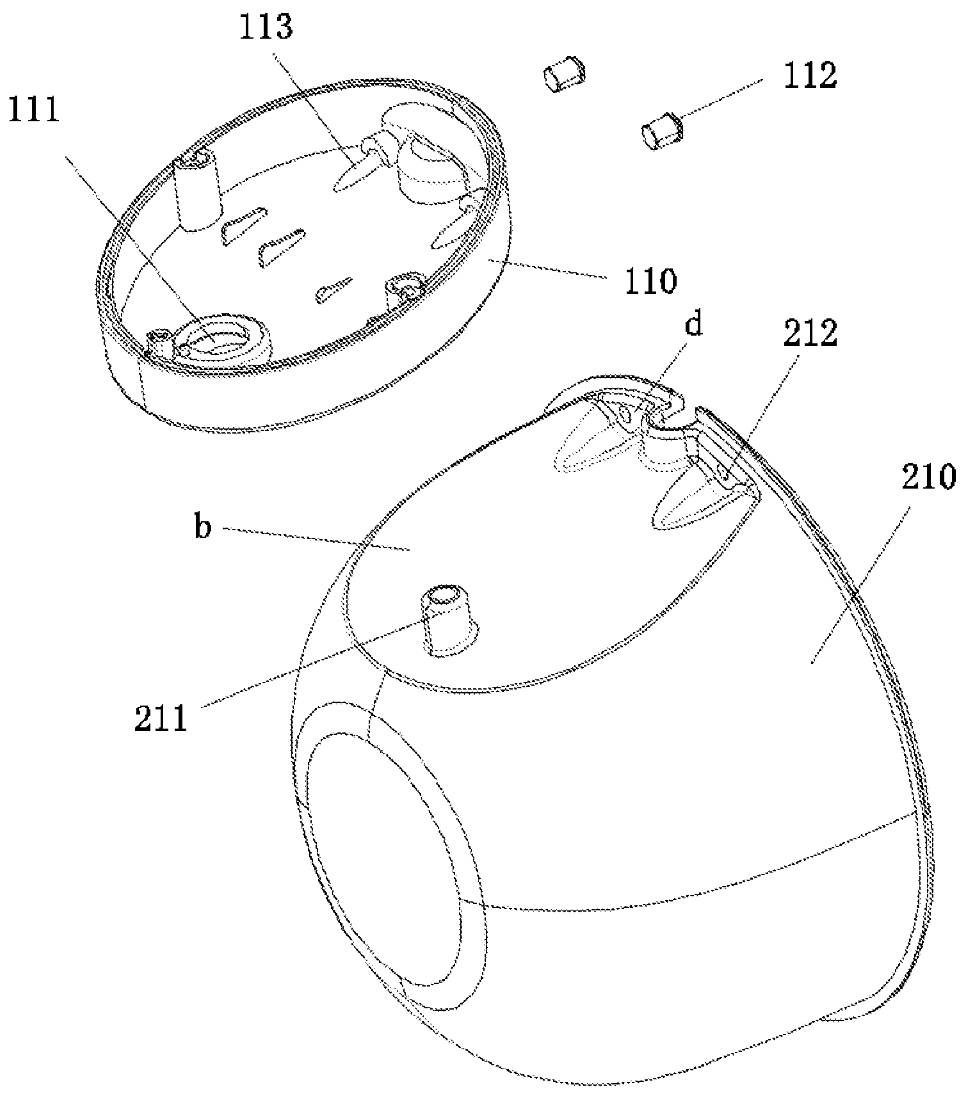
FIG. 7 is a schematic structural schematic diagram of a housing and a milk bowl.
Figure 8:
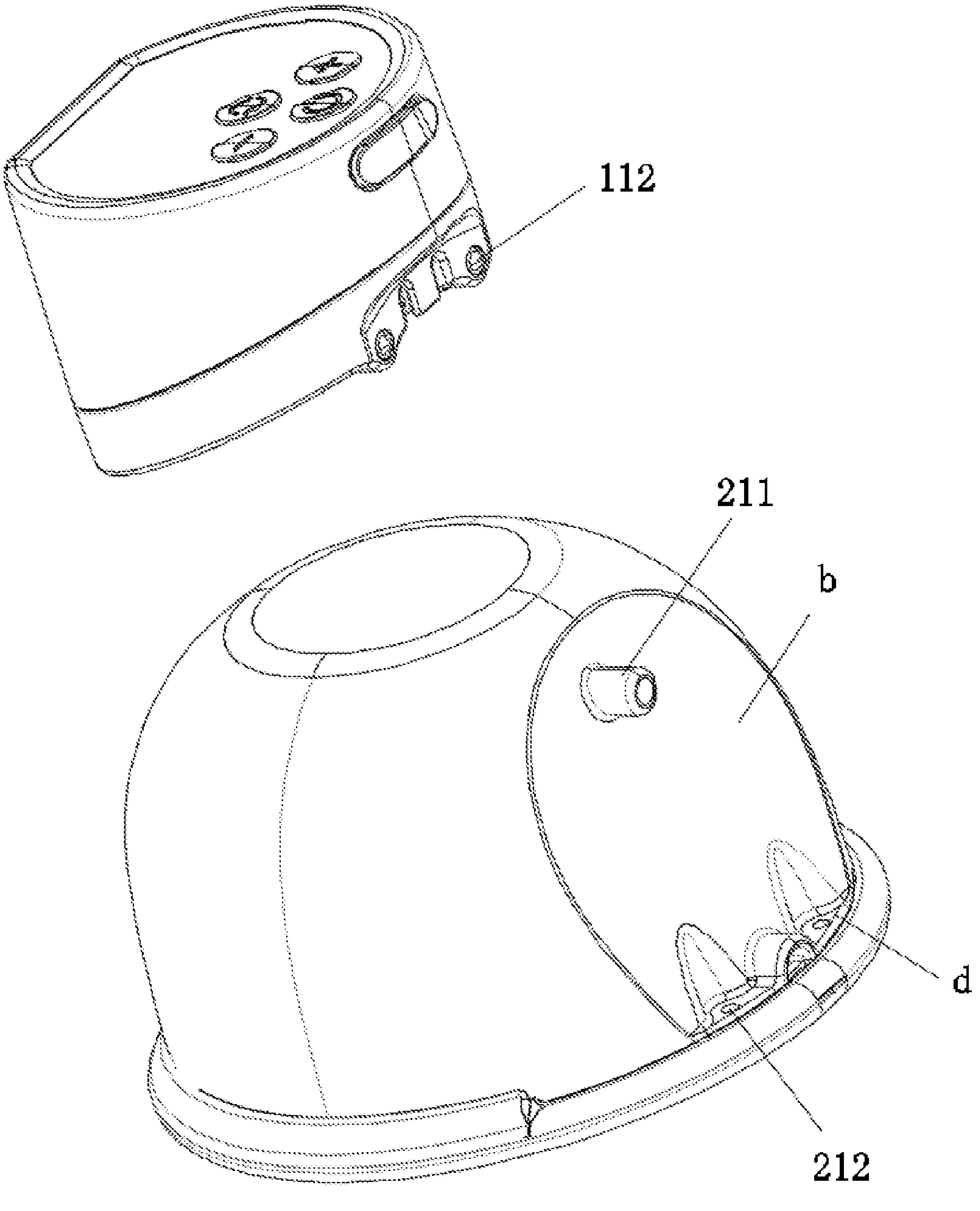
FIG. 8 is a schematic structural diagram of one perspective view of the main body and the milk collector.

In the present embodiment, as shown in FIG. 7 and FIG. 8, the milk bowl 210 is provided with a connecting post 211, the housing 110 is provided with a connecting groove 111, and the connecting post 211 is detachably engaged to the connecting groove 111. The housing 110 is provided with an elastic protrusion 112, and the milk bowl 210 is provided with a groove 212 corresponding to the elastic protrusion 112. An included angle is formed between the engagement direction of the connecting post 211 relative to the connection groove 111 and the engagement direction of the elastic protrusion 112 relative to the groove 212. When the housing 110 is assembled with the milk bowl 210, the connecting post 211 is fittingly engaged to the connecting groove 111 to spatially communicate the membrane 260 with the air pump 130. In addition, the elastic protrusion 112 is placed in the groove 212, and the connecting post 211 is connected to the connecting groove 111. The engagement of the connecting post 211 relative to the groove 111 combined with the engagement of the elastic protrusion 112 relative to the groove 212 makes the assembly between the milk bowl 210 and the main body 100 very stable, and the milk bowl 210 is not easy to detach relative to o the main body 100. In addition, when the milk bowl 210 is assembled with the main body 100, a cooperation between the elastic protrusion 112 and the groove 212 will make a specific sound, such as "click", to give feedback to the user and let the user know that it has been assembled properly.

More specifically, the included angle between the engagement direction of the connecting post 211 relative to the connecting groove 111 and the engagement direction relative to the elastic protrusion 112 and the groove 212 is 90 degrees, so that when assembled, the connecting post 211 and the connecting groove 111 are opposite to the main body 100. The assembly of the main body 100 and the milk collector 200 acts as a guiding function. The main body 100 and the milk collector 200 can be assembled along the engagement direction of the connecting post 211 relative to the connecting groove 111, and the main body 100 and the milk collector 200 are limited to detach along the engagement direction of the connecting post 211 and the connecting groove 111. Similarly, the elastic protrusion 112 and the groove 212 limit the detachment of the main body 100 and the milk collector 200 at different positions in the same direction.

In other embodiments, the connecting post 211 and the connecting groove 111 are installed on different planes from the elastic protrusion 112 and the groove 212, and the two installation planes are arranged at an included angle.

In other embodiments, the housing 110 may also be provided with the connecting post 211, and the milk bowl 210 may be provided with the connecting groove 111. The milk bowl 210 may also be provided with the elastic protrusion 112, and the housing 110 may be provided with the groove 212 corresponding to the elastic protrusion. 112. In addition, the included angle between the engagement direction of the connecting post 211 relative to the connection groove 111 and the engagement direction of the elastic protrusion 112 relative to the groove 212 can also be 45 degrees, 60 degrees, 70 degrees, 75 degrees, 80 degrees, 85 degrees, etc.

Figure 9:
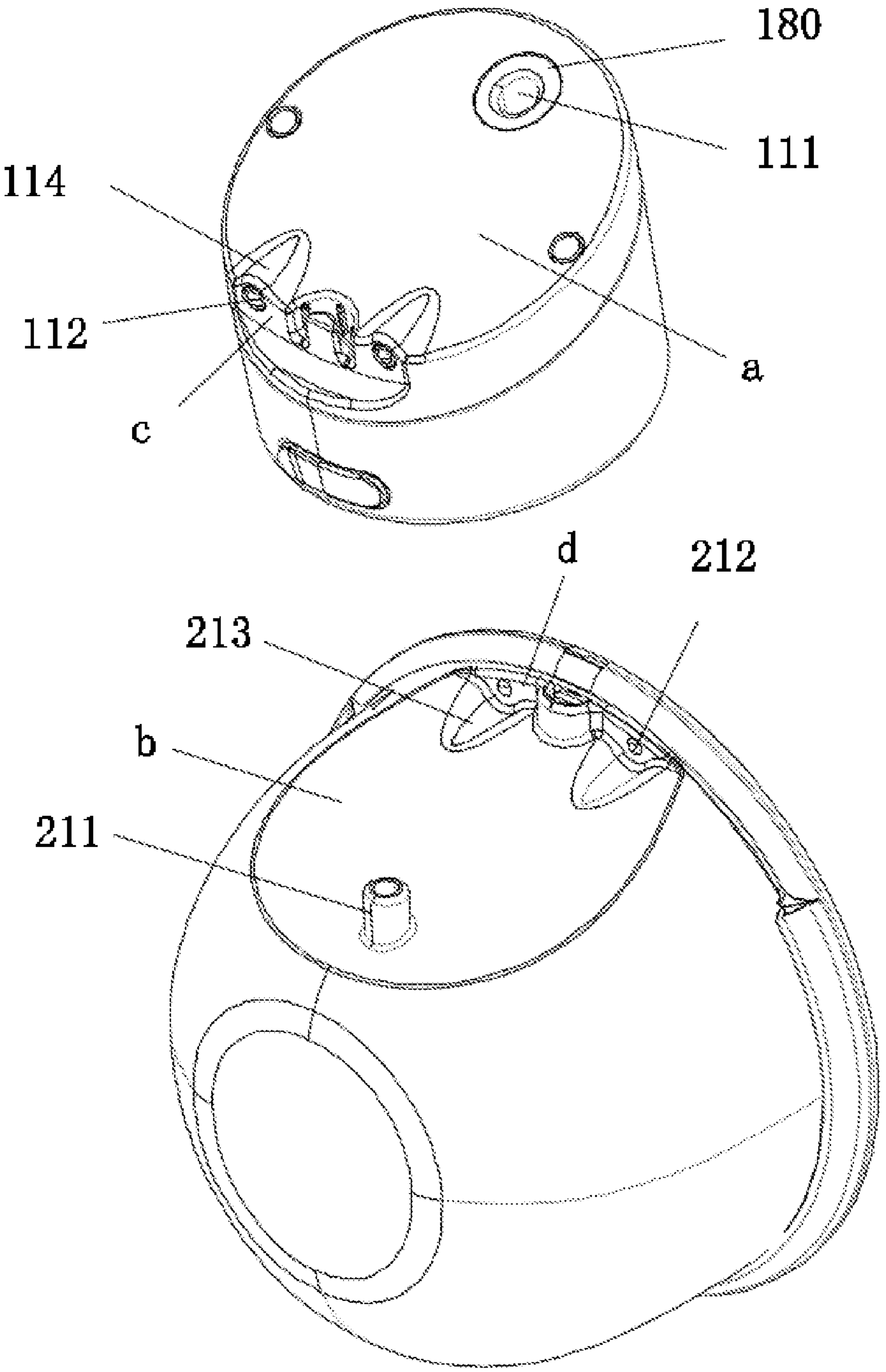
FIG. 9 is a 1 schematic structural diagram of another perspective of the main body and the milk collector.

As a preferred embodiment, as shown in FIG. 9, an elastic sealing member 180 is provided on the groove wall surface of the connecting groove 111. By providing the elastic sealing member 180, the seal and the tightness are improved after the connecting post 211 is engaged to the connection groove 111.

In the present embodiment, there are two elastic protrusions 112 and two grooves 212. In this way, the connecting post 211 and the connecting groove 111 form a fixed point, and each pair of the elastic protrusions 112 and the grooves 212 form a fixed point. In this way, the assembly between the milk bowl 210 and the main body 100 is more stable through the three-point limit. In the three connecting and assembling points, the connecting and assembling points of the connecting post 211 and the connecting groove 111 are not in the same plane as the other two connecting and assembling points, and the two pairs of elastic protrusions 112 and the two pairs of grooves 212 can be formed on the milk bowl 210 and the main body 100. The limit in the same direction as the engagement direction of the connecting post 211 relative to the connecting groove 111 can also form a limit in the direction of the line between the two pairs of elastic protrusions 112 and the groove 212, and can also limit the milk bowl 210 moving along the insertion direction of the elastic protrusion 112 and the groove 212 relative to the housing 110, and can restrict the milk bowl 210 from detaching from the housing 110 along the direction. Preferably, the connecting post 211 and the connecting groove 111 are located on a center line of a connecting line between the two pairs of elastic protrusions 112 and the grooves 212. In some embodiments, other numbers of elastic protrusions 112 and grooves 212 may also be provided.

For ease of understanding, as shown in FIG. 8 and FIG. 9, a surface where the connecting post 211 and the connecting groove 111 are located is defined as a first contact surface between the housing 110 and the milk bowl 210, and a surface where the elastic protrusion 112 and the groove 212 are located is defined as a second contact surface between the housing 110 and the milk bowl 210. Specifically, in the present embodiment, one surface of the first contact surface at the housing 110 is defined as a first surface a, and another surface of the first contact surface at the milk bowl 210 is defined as a second surface b. One surface of the second contact surface at the housing 110 is defined as a third surface c, and another surface of the second contact surface at the milk bowl 210 is defined as a fourth surface d.

In the present embodiment, in order to further improve the assembly stability between the milk bowl 210 and the main body 100, the connecting post 211 is located on an end of the second surface b away from the fourth surface d, and the connecting groove 111 is correspondingly located on an end of the first surface a away from the third surface c.

As shown in FIG. 7, the housing 110 is provided with a spring groove 113, and the elastic protrusion 112 includes: a protruding piece whose head can extend out of the spring groove 113 and whose tail is restricted in the spring groove 113, and a spring (not shown) disposed in the spring groove 113, of which one end abuts against the protrusion, and of which another end abuts against the inner wall of the spring groove 113. The head of the protruding piece is spherical, and the groove 212 is a spherical groove 212 adapted thereto.

When the housing 110 is assembled with the milk bowl 210, the head of the elastic protrusion 112 is pressed by the outer wall of the second contact surface of the milk bowl 210, at this time the elastic protrusion 112 retracts into the spring groove 113, and the spring is under compression state. When the housing 110 moves to the position where the elastic protrusion 112 is aligned with the groove 212, since the head of the elastic protrusion 112 is no longer pressed by the outer wall of the second contact surface of the milk bowl 210, the returned spring pushes out the elastic protrusion 112, at this time the head of the elastic protrusion 112 pushes into the groove 212 of the milk bowl 210, and the cooperation between the elastic protrusion 112 and the groove 212 will make a specific sound, thereby providing feedback to the user and letting the user know it has been assembled properly.

In other embodiments, the elastic protrusion 112 and the groove 212 can also be arranged at other positions, and the specific structure can also be modified, as long as the elastic protrusion 112 can stretch in and out of the groove 212.

Further, as shown in FIG. 9, the outer wall of the spring groove 113 is formed with an arc-shaped protrusion 114 on the first contact surface, and the milk bowl 210 is formed with a corresponding arc-shaped groove 213 on the first contact surface. The arc-shaped protrusion 114 and the arc-shaped groove 213 can guide the assembly of the milk bowl 210 and the housing 110.

As shown in FIG. 5, in the present embodiment, the housing 110 is provided with a charging hole 115, and the charging member 121 on the circuit board 120 is connected to an external power source through the charging hole 115 so as to charge the battery 150.

A dust plug 160 is provided at the charging hole 115, and the dust plug 160 is used to plug into the charging hole 115. When not charging, the dust plug 160 can be inserted into the charging hole 115 to prevent the charging hole 115 from dust and avoid affecting subsequent charging.

Referring to FIG. 3 and FIG. 5, a plurality of buttons 170 correspondingly connected to the circuit board 120 are provided on an upper side of the housing 110, including a switch key 171, a mode key 172, a gear increase key 173 and a gear reduce key 174. Pressing and holding the on/off key 171 circularly can control the power on or off of the circuit board 120 to enter the power-on mode or the power-off mode. In the power-on mode, pressing the mode key 172 cyclically can switch pausing/starting the air pump 130 cyclically. In the power-on mode, pressing the gear increase key 173 can control the air pressure of the air pump 130 to increase, so that the vacuuming intensity and pressurization intensity of the air pump 130 become greater. In the power-on mode, pressing the gear down key 174 can control the air pressure of the air pump 130 to decrease, so that the vacuuming intensity and pressurization intensity of the air pump 130 decrease.

In the present embodiment, the color of the milk bowl 210 is transparent, and the outer wall of the milk bowl 210 is provided with a capacity scale (not shown), which is convenient for observing the milk capacity contained in the milk storage cavity 220 in the milk bowl 210, and reminds the user whether to continue pumping milk.

Referring to FIG. 3, the side of the milk bowl 210 facing away from the breast shield 230 has a placement plane 214, and the placement plane 214 is planar, so that the milk bowl 210 can be placed on the desktop through the placement plane 214.

Referring to FIG. 4, the breast shield 230 is funnel-shaped, the side of the breast shield 230 facing the milk bowl 210 has a connector 231, and the connector 231 is used for detachably engaged to the suction port 241 of the airway connector 240. A sealing ring 232 is sleeved on the connector 231, and the sealing ring 232 is used to seal the gap between the connector t 231 and the airway connector 240, so as to ensure the tightness of the connection between the breast shield 230 and the airway connector 240.

The breast shield 230 is provided with an annular mounting groove 233 facing a circumferential edge of the milk bowl 210, and the mounting groove 233 is detachably engaged to the engagement flange 218 of the milk bowl 210. It can be understood that, in other embodiments, the breast shield 230 and the milk bowl 210 may also be connected to each other in other detachable ways, such as magnetic connection, screw connection, etc., which are not limited herein. When the milk in the milk storage cavity 220 needs to be poured out, the breast shield 230 can be disassembled and detached from the milk bowl 210. When pumping milk is needed, the breast shield 230 can be connected with the milk bowl 210.

The breast shield 230 has a liquid inlet groove 234 that is hollow. When the liquid inlet groove 234 is connected to a milk inlet of the airway connector 240, an end of the breast shield 230 facing away from the milk bowl 210 is used to attach to the breast. When the airway connector 240 is evacuated, the liquid inlet groove 234 forms a negative pressure to pump the milk in the mammary gland. The milk flows to the milk inlet of the airway connector 240 through the liquid inlet groove 234, and then flows to the milk storage cavity 220 in the milk bowl 210 through the one-way valve 250. Specifically, in the present embodiment, the one-way valve 250 is a duckbill valve.

The above is only used to illustrate the technical solution of the present disclosure and not to limit it. Other modifications or equivalent replacements made by those skilled in the art to the technical solution of the present disclosure, as long as they do not deviate from the spirit and scope of the technical solution of the present invention, shall be covered by the claims of the present disclosure.

What is claimed is:

1. A breast pump, including:

a milk bowl, a breast shield detachably connected to the milk bowl, wherein a milk storage cavity for storing milk is defined by the breast shield and the milk bowl, and a main body detachably connected to the milk bowl, wherein the main body includes a housing detachably connected to the milk bowl, and an air pump disposed in the housing and used for generating negative pressure; and wherein the milk bowl is provided with a milk outlet in fluid communication with the milk storage cavity, the housing is provided with a hole plug engaged to the milk outlet, and the hole plug is configured to at least partially seal the milk outlet to form a ventilation channel through which outside air communicates with the milk storage cavity to facilitate milk flowing into the milk storage cavity, and to prevent contamination and spillover.

2. The breast pump according to claim 1, wherein, when the breast shield is attached to a breast, the milk outlet faces upward.

3. The breast pump according to claim 1, wherein the milk outlet is arranged on an outer edge of the milk bowl.

4. The breast pump according to claim 1, wherein the milk outlet has an inner wall surface that is arc-shaped, or the hole plug has an outer wall surface that is arc-shaped and corresponds to the milk outlet.

5. The breast pump according to claim 1, wherein the milk outlet is semi-cylindrical shaped, or the hole plug is semi-cylindrical shaped.

6. The breast pump according to claim 1, wherein, when the housing is assembled with the milk bowl, an outer wall surface of the hole plug is spaced apart from an inner wall surface of the milk outlet.

7. The breast pump according to claim 1, wherein the housing is provided with a positioning groove, the hole plug extends from a groove bottom of the positioning groove, the milk bowl is provided with a hole wall forming the milk outlet, and, when the housing is assembled with the milk bowl, the hole plug is engaged to the milk outlet, and the hole wall is engaged to the positioning groove.

8. The breast pump according to claim 7, wherein, when the housing is assembled with the milk bowl, the hole wall fits into the positioning groove.

9. The breast pump according to claim 7, wherein a side wall of the positioning groove is arc shaped, and an outer wall surface of the hole wall has an arc-shaped outer wall surface corresponding to the side wall of the positioning groove.

10. The breast pump according to claim 7, wherein the positioning groove is semi-cylindrical shaped, and the hole wall is semi-cylindrical shaped corresponding to a side wall of the positioning groove.

11. The breast pump according to claim 7, wherein a side wall of the positioning groove is provided with a positioning rib, and, when the hole plug is inserted into the milk outlet, the positioning rib abuts against an outer wall surface of the hole wall.

* * * * *